United States Patent
Rich et al.

(10) Patent No.: US 8,282,570 B2
(45) Date of Patent: Oct. 9, 2012

(54) SIDESTREAM GAS SAMPLING SYSTEM WITH DETACHABLE SAMPLE CELL

(75) Inventors: David R Rich, Glastonbury, CT (US); Anthony T Pierry, Plantsville, CT (US); Brian M Fudge, Middletown, CT (US); John L Sandor, North Haven, CT (US); John A Triunfo, Jr., Fairfield, CT (US)

(73) Assignee: RIC Investments, LLC, Wilmington, DE (US)

( * ) Notice: Subject to any disclaimer, the term of this patent is extended or adjusted under 35 U.S.C. 154(b) by 1284 days.

(21) Appl. No.: 12/025,411

(22) Filed: Feb. 4, 2008

(65) Prior Publication Data

US 2008/0200825 A1    Aug. 21, 2008

Related U.S. Application Data

(63) Continuation of application No. 10/384,329, filed on Mar. 7, 2003, now Pat. No. 7,341,563.

(60) Provisional application No. 60/370,002, filed on Apr. 4, 2002.

(51) Int. Cl.
    *A61B 5/08* (2006.01)
(52) U.S. Cl. .......... 600/532; 73/23.3
(58) Field of Classification Search ........ 600/529, 600/531–533, 538, 476, 477; 73/23.3, 23.35, 73/23.36, 23.37, 23.41; 422/84; 436/136, 436/165
See application file for complete search history.

(56) References Cited

U.S. PATENT DOCUMENTS

| | | | |
|---|---|---|---|
| 4,177,381 A | 12/1979 | McClatchie et al. | |
| 4,692,621 A | 9/1987 | Passaro et al. | |
| 4,859,858 A | 8/1989 | Knodle et al. | |
| 4,859,859 A | 8/1989 | Knodle et al. | |
| 4,914,720 A | 4/1990 | Knodle et al. | |
| 4,958,075 A | 9/1990 | Mace et al. | |
| 5,282,473 A | 2/1994 | Braig et al. | |
| 5,789,660 A | 8/1998 | Kofoed et al. | |
| 5,932,877 A | 8/1999 | Braig et al. | |
| 6,126,610 A | 10/2000 | Rich et al. | |
| 6,191,421 B1 | 2/2001 | Yamamori et al. | |
| 6,216,692 B1 | 4/2001 | Todokoro et al. | |
| 6,258,040 B1 | 7/2001 | Yamamori et al. | |
| 6,312,389 B1 | 11/2001 | Kofoed et al. | |
| 6,325,978 B1 | 12/2001 | Labuda et al. | |
| 6,512,581 B1 | 1/2003 | Yamamori et al. | |
| 6,599,253 B1 | 7/2003 | Baum et al. | |
| 6,616,896 B2 | 9/2003 | Labuda et al. | |
| 6,632,402 B2 | 10/2003 | Blazewicz et al. | |

OTHER PUBLICATIONS

Solomon, "A Reliable, Accurate CO2 Analyzer for Medical Use," Hewlett-Packard Journal, Sep. 1981, pp. 3-21.

Novametrix Medical Systems, Inc., Movametrix Capnogard Model 1250 End Tidal Monitor Operating Manual, 1986, Wallingford, Connecticut.

*Primary Examiner* — Navin Natnithihadha

(57) ABSTRACT

A sidestream sampling system includes a sidestream gas measurement assembly and a sample cell configured to be assembled therewith. The sidestream gas measurement assembly includes a receptacle for removably receiving at least a portion of the sample cell. The sample cell is coupled to a sampling tube that is configured to communicate with an airway of an individual. When the sample cell is assembled with the sidestream gas measurement assembly, a window of the sample cell is oriented toward a corresponding source and/or detector of the sidestream gas measurement assembly to facilitate monitoring of an amount of at least one gas or vaporized material in an individual's respiration.

20 Claims, 12 Drawing Sheets

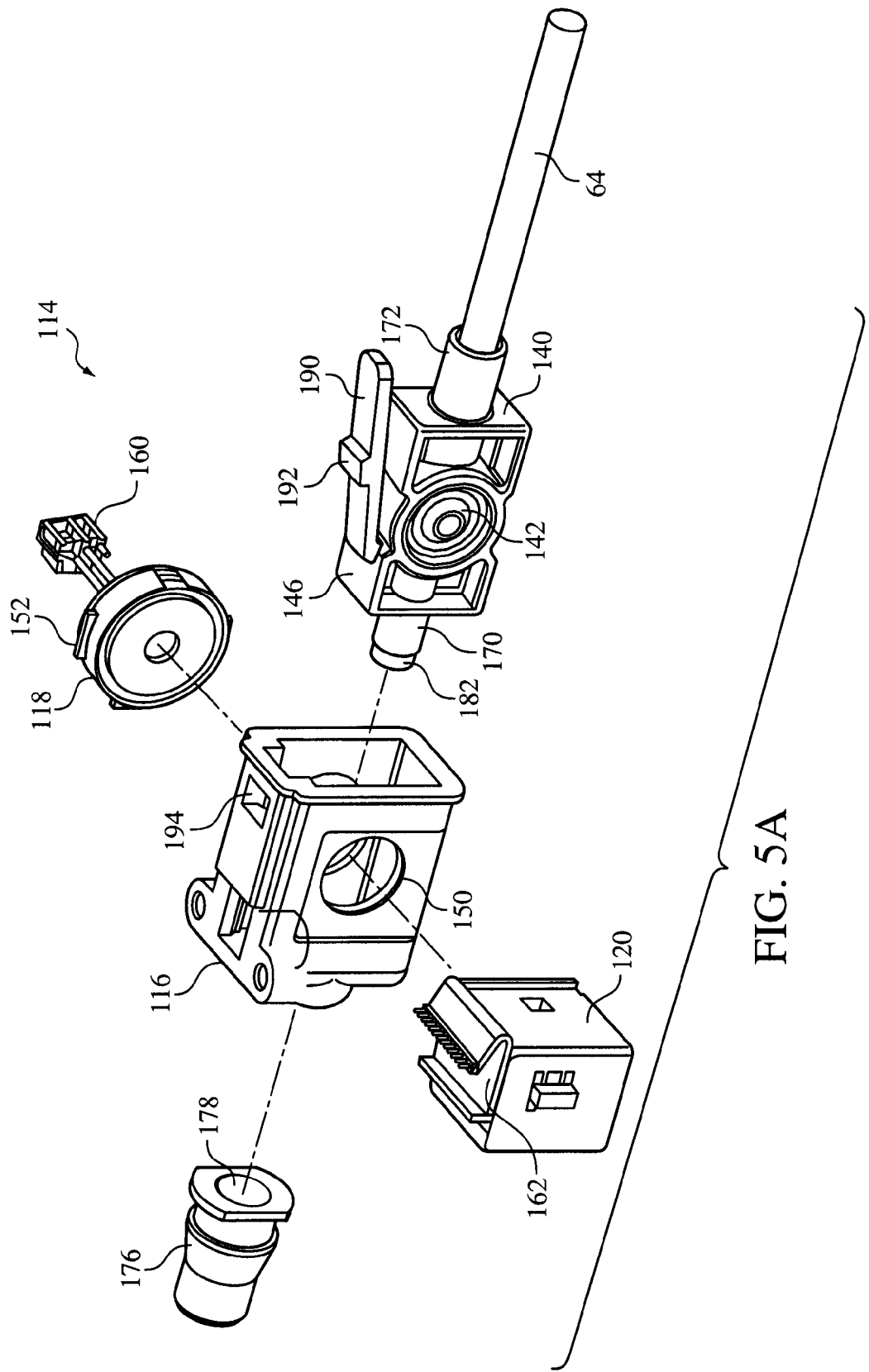

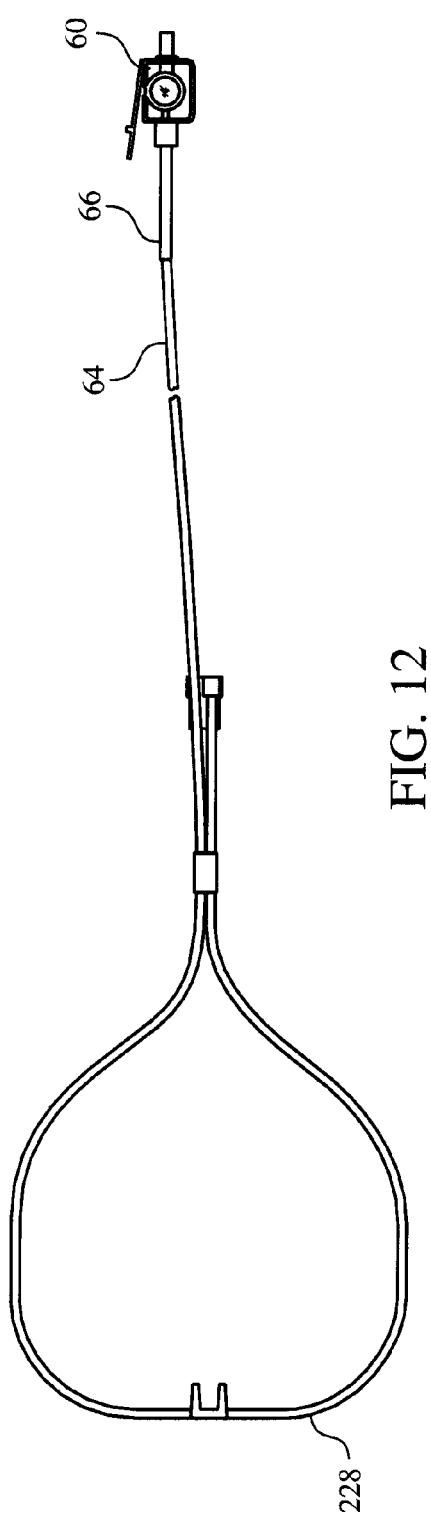
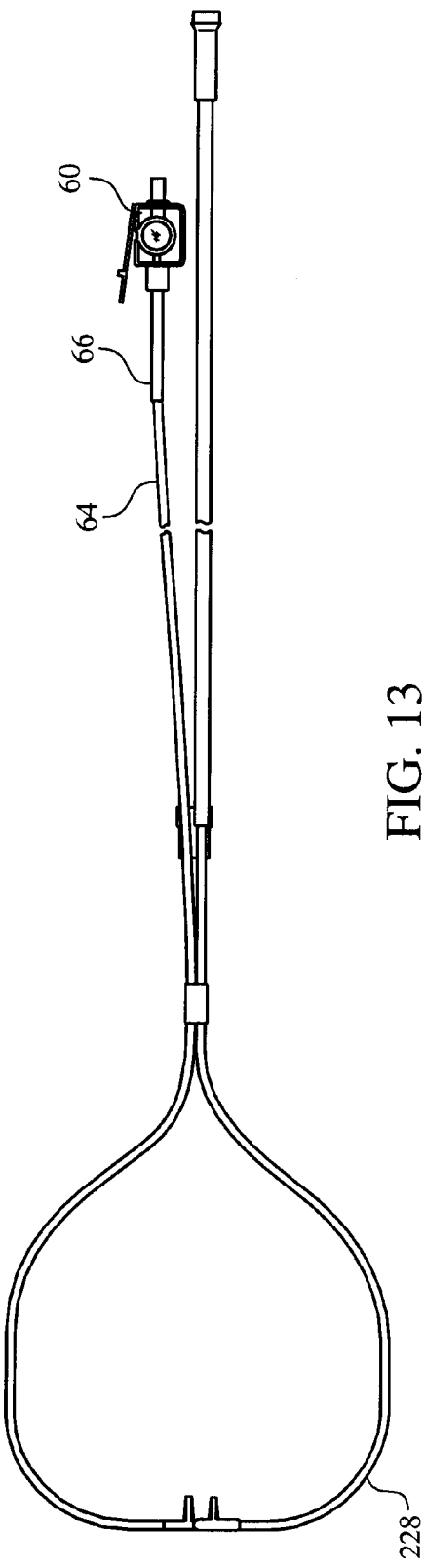

SIDESTREAM GAS SAMPLING SYSTEM WITH DETACHABLE SAMPLE CELL

CROSS-REFERENCE TO RELATED APPLICATIONS

This application is a Continuation under 35 U.S.C. §120 of U.S. patent application Ser. No. 10/384,329, filed Mar. 7, 2003, which claims priority under 35 U.S.C. §119(e) from provisional U.S. patent application No. 60/370,002, filed Apr. 4, 2002.

BACKGROUND OF THE INVENTION

1. Field of the Invention

The present invention relates to a detachable sample cell for a sidestream respiratory gas sampling system, and, in particular, to a detachable sample cell that is readily removable from and replaceable in a sidestream respiratory gas sampling system.

2. Description of the Related Art

It is well-known by those skilled in the art that gas analyzers of the non-dispersive infrared (NDIR) type operate on the principle that the concentration of specific gases can be determined by (a) directing infrared radiation through a gas sample, (b) filtering this infrared radiation to minimize the energy outside the band absorbed by a specific gas in the gas sample, (c) measuring the radiation impinging upon a detecting device after having passed through the gas sample, and (d) relating a measure of the infrared absorption of the gas to the concentration of one or more specific gases being monitored. Gases that may be measured exhibit increased absorption (and reduced transmittance) at specific wavelengths in the infrared spectrum such that the greater the gas concentration, the greater the absorption, and, conversely, the lower the transmittance of the infrared radiation.

NDIR gas analyzers are widely used in medical applications and are typically categorized into two different types: (1) "diverting" or "sidestream" gas sampling systems; and (2) a "non-diverting" or "mainstream" gas sampling systems. A mainstream gas sampling system includes a sample cell that is disposed along the main path of a breathing circuit through which a patient's respiratory gases flow. As a result, the patient's inspired and expired respiratory gases pass through a sample cell, which is also known as a "cuvette". A gas sensing system, which includes the elements necessary for monitoring respiratory gases such as a radiation source and detector, are coupled to the sample cell to measure the constituents of gas passing through the sample cell. An example of such a conventional mainstream Gas Measurement System is shown in U.S. Pat. No. 4,914,720 issued to Knodle et al.

A sidestream type of gas sampling system transports a portion of sampled gases from the sampling site, which is typically a breathing circuit coupled to the patient's airway or directly at the patient's airway, through a sampling tube to the sample cell, where the constituents of the gas are measured by a gas sensing system. Gases are continuously aspirated from the sample site, through the sampling tube, and into the sample cell, which is located within a gas measurement instrument. Gases are commonly sampled at flow rates ranging from about 50 ml/min to about 250 ml/min. The optical and electronic components associated with the sample cell for measuring the gas passing therethrough are positioned in the monitor a distance away from the patient's airway or a respiratory circuit. Examples of conventional sidestream gas sampling systems are taught in U.S. Pat. Nos. 4,692,621 to Passaro et al.; 4,177,381 to McClatchie; 5,282,473 to Braig et al.; and 5,932,877 also issued to Braig et al.

Conventionally, the sampling ports used by sidestream gas sampling systems are located in a wall of the respiratory circuit or an airway adapter therefor. The location of the sampling port along a breathing circuit may range anywhere from an elbow connected to an endotracheal tube to a wye connector at the opposite end of a breathing circuit. For example, the sampling port may be placed on the ventilator side of an in-line filter or heat-moisture exchanger (HME). This results in a drier sampling tube but with the inherent risk of significant distortion of the capnographic waveform and lower end-tidal values.

It is also well known in the art to locate the sampling port on the patient side of the in-line filter. However, there is a possibility of an accumulation of condensate and/or patient secretions in this configuration for a sidestream sampling system. Condensation from a humidified sample gas, in combination with patient secretions, can block and contaminate the sampling tube, which may necessitate frequent replacement thereof. To protect the sample cell from condensate, it is known to make the sampling tube permeable to water vapor, for example by using dehumidifying tubing, such as NAFION.®. brand tubing. It is also known to provide a water trap positioned at some point along the length of the sampling tube, a water filter also positioned along the sampling tube, or any combination of the dehumidification tubing, water trap, and water filter. The effectiveness of water traps and water filters vary between manufacturers, but no water trap or water filter is immune to eventual clogging and distortion of the capnographic waveform, particularly if preventive maintenance is inadequate.

Additionally, sources of leaks external to the gas monitor, such as loose fittings, cracked or slit sampling tubes, cracked sample filters, and cracked airway adapters, along with sources of leaks internal to the monitor, such as partial disconnection, are known to cause significant artifact in the capnogram output by conventional sidestream gas sampling systems. Leaks and obstructions can occur at any of the numerous connection points and tubes within a sidestream gas sampling system. As it may be difficult or impossible to calibrate for such artifacts, leaks, and obstructions, the capnographic waveforms and end-tidal measurements that are generated by use of sidestream analyzers may provide values that are significantly different from the actual values, which may, in turn, pose a potential hazard to the patient.

While more recent sidestream gas sampling system designs employ sampling ports that are located in the center of the adapter and, thus, along the flow path therethrough rather than at a wall thereof and, therefore, are less likely to aspirate secretions within a patient's respiration, they are still susceptible to the problems outlined above.

These problems are further exacerbated by the fact that the sample cells of sidestream analyzers are reusable and nondisposable, with windows that are formed from sapphire or other expensive materials. Thus, over time, condensation and contamination are likely to build up within such sample cells, reducing their performance over time. While the reusable sample cells of some sidestream analyzers may be removed therefrom for cleaning, the cleaning process is often avoided due to the high costs associated with replacing such sample cells. As a result, following the cleaning of such a sample cell, the accuracy of measurements obtained therewith diminishes over time.

Currently, the use of sidestream gas monitoring requires that careful attention be paid to the physical setup both external and internal to the monitor, and that care be taken in interpreting the capnographic waveform.

Given these problems with sidestream capnography, it is desirable to provide a sidestream gas sampling system that (a) is less prone to both internal and external leaks and obstructions, (b) provides data that more accurately reflects the true capnographic waveform of a patient's respiration, (c) is more robust with respect to accumulation of condensate and patient secretions, and (d) facilitates an easy determination of problems and corrective actions at the point of care should any of the above-noted problems occur with the sampling tube and/or the sample cell.

SUMMARY OF THE INVENTION

Accordingly, it is an object of the present invention to provide a sidestream gas sampling system and method that overcomes the shortcomings of conventional sidestream gas sampling systems and method. This object is achieved according to one embodiment of the present invention by providing a sidestream gas sampling system that includes a sidestream gas measurement assembly and a sample cell assembly adapted to be coupled to the sidestream gas measurement assembly. The sidestream gas measurement assembly includes a housing, a radiation source and detector disposed in the housing, a receptacle defined in the housing, and a first alignment mechanism associated with the receptacle. The sample cell assembly includes a sampling tube have a first end portion adapted to be disposed in fluid communication with an airway of a patient and a second end portion. The sampling tube carries a gas sample from the first end portion to the second end portion. The gas sample is a fraction of a total gas flow to or from such a patient. The sample cell assembly also includes a sample cell having a first end portion coupled to the second end portion of the sampling tube, a sample chamber defined in the sample cell for receiving a respiratory sample from such a patient via the sampling tubing, and a first window defined in the sample cell. A second alignment mechanism is associated with the sample cell such that the first alignment mechanism and the second alignment mechanism cooperate to enable the sample cell to be inserted into the receptacle in a proper orientation.

The sidestream gas measurement assembly may be a component of a multi-parameter system, for example, a system that is capable of monitoring a combination of respiratory gases and/or vapors, a respiratory gas or vapor and respiratory flow, a combination thereof, or the like. Also, the sample cell may be included as part a standalone sidestream gas monitoring system or to may be retrofit on an existing sidestream gas monitoring system or on a system that was originally designed for mainstream-only operation.

It is a further object of the present invention to provide a method of performing a sidestream respiratory analysis that includes the steps of (1) providing a sample cell assembly comprising (a) a sampling tube have a first end portion and a second end portion, and (b) a sample cell coupled to the second end portion of the sampling tube, (2) placing a first end portion of the sampling tube in fluid communication with an airway of a patient, (3) carrying a gas sample from the first end portion to the second end portion, wherein the gas sample is a fraction of a total gas flow to or from such a patient, (4) orienting the sample cell such that a first alignment mechanism associated with the receptacle is aligned with a second alignment mechanism associated with a receptacle defined in a housing of a sidestream gas measurement assembly, (5) inserting the sample cell into the receptacle responsive to the first alignment mechanism and the second alignment mechanism being properly oriented relative to one another, and (6) analyzing a parameter of the gas sample using the sidestream gas measurement assembly. It is to be understood that these steps need not be carried out in the order given above.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 5A and 5B are exploded perspective first and second side views of an exemplary embodiment of a gas sensing assembly;

FIG. 12 is a side view of a sampling set for non-intubated patients, without oxygen delivery, that includes a sample cell, a filter, and a nasal cannula; and FIG. 13 is a side view of an exemplary sampling set for non-intubated patients with oxygen delivery, including a sample cell, a filter, a nasal cannula, and an optional port for oxygen delivery.

DETAILED DESCRIPTION OF THE EXEMPLARY EMBODIMENTS

Figure 1A:
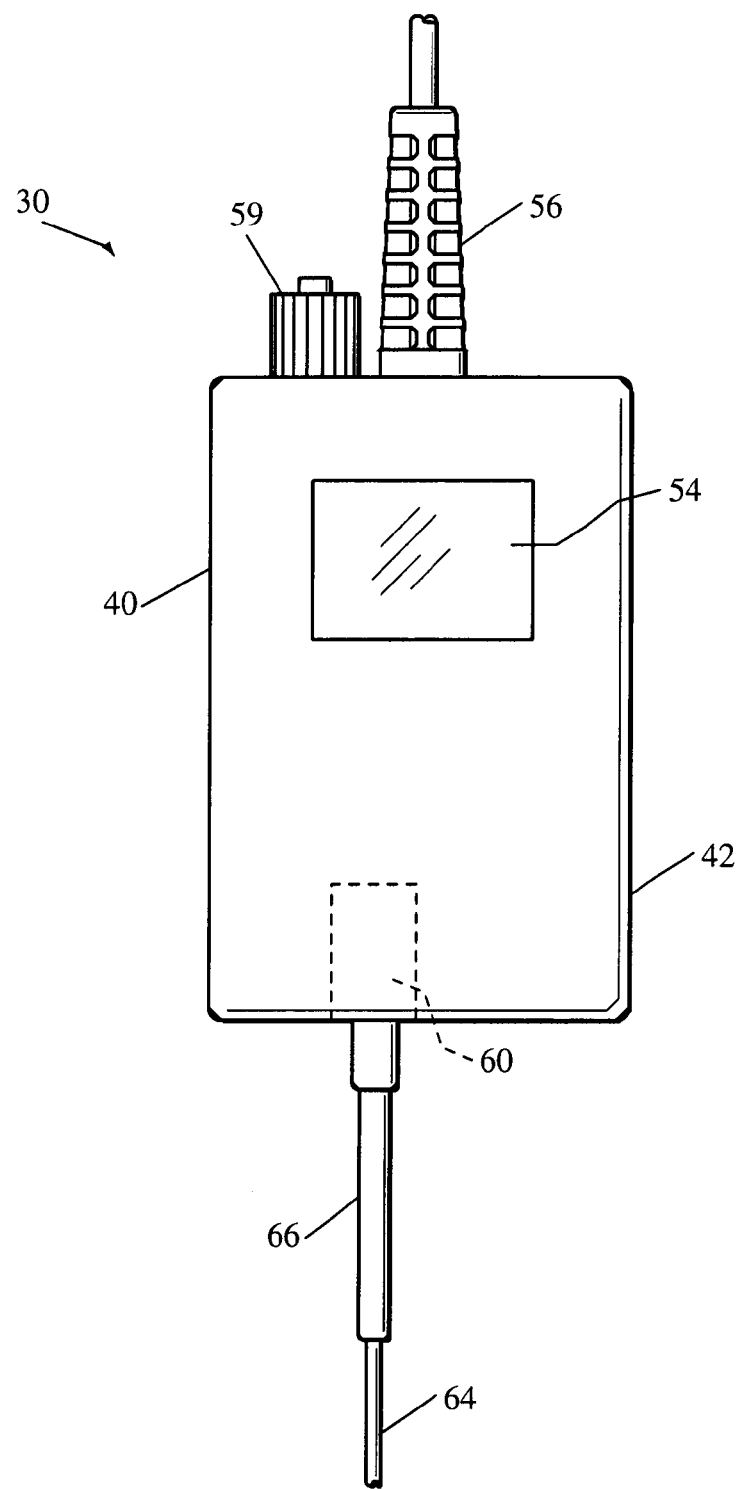
FIG. 1A is a top view of a first embodiment of a stand-alone sidestream gas sampling system according to the principles of the present invention.
Figure 1B:
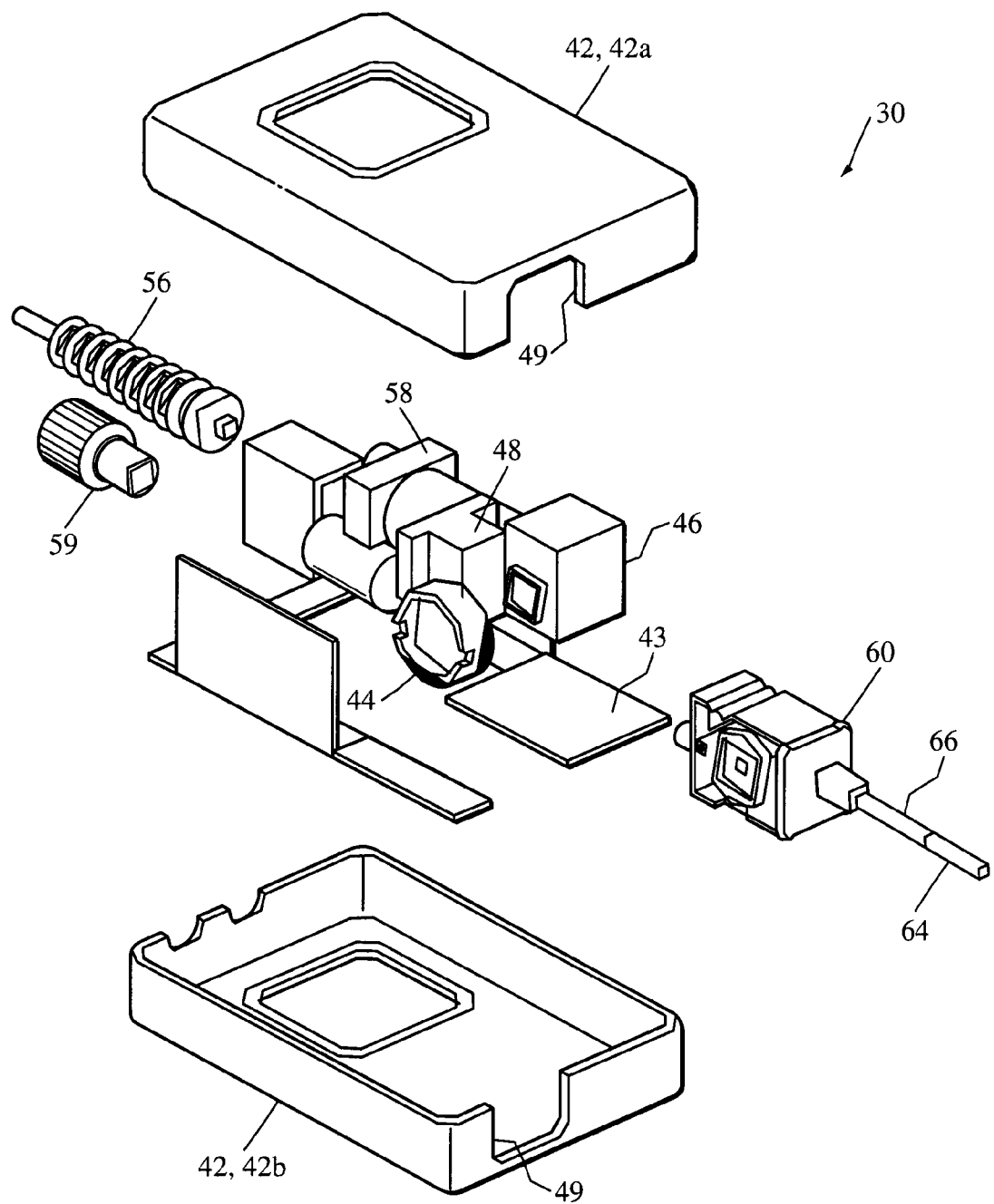
FIG. 1B is an exploded view of the sidestream gas measurement assembly in the sidestream gas sampling system shown in FIG. 1A.

FIGS. 1A and 1B illustrate a first embodiment of a stand-alone sidestream gas sampling system 30 according to the principles of the present invention. Sidestream gas sampling system 30 includes a sidestream gas measurement assembly 40 and a sample cell 60 that selectively attaches to the sidestream gas measurement assembly. Sidestream gas measurement assembly 40 is shown in exploded view in FIG. 1B.

Sidestream gas measurement assembly 40 includes a housing 42, which, in an exemplary embodiment of the present invention, is defined by two housing portions 42a and 42b that are adapted to be joined together in an assembled relation. The various elements of sidestream gas measurement assembly 40 may be at least partially contained within or otherwise carried by housing 42, which is configured to receive a substrate 43 on which one or more of the components of the sidestream gas measurement assembly can be mounted. A radiation source 44 and a radiation detector 46 are disposed in the housing in optical alignment so that radiation emitted by the source is received by the detector after passing through the gas contained in sample cell 60.

In an exemplary embodiment of the present invention, radiation source 44 includes an infrared emitter, a mounting, a parabolic mirror, and a window of an infrared radiation-transmitting material, such as sapphire. Radiation detector 46 comprises a window of infrared radiation-transmitting material, a beam splitter, one or more filters, and data and reference detectors. Radiation detector 46 may also include electronics that facilitate monitoring and/or temperature control of the data and reference detectors thereof.

Housing 42 also includes a receptacle 48 that is sized and configured to receive at least a portion of the sample cell for securing the sample cell to the housing. A slot 49 is provided in an exterior of the housing to allow the sample cell to engage the receptacle. It should be noted that the present invention contemplates that receptacle 48 can be defined by housing 42, rather than as a separate component as shown in FIG. 1B. That is, slot 49 can be part of the receptacle for removeably attaching the sample cell to the sidestream gas measurement assembly.

When sample cell 60 is assembled with sidestream gas measurement assembly 40 according to the present invention by insertion of the sample cell at least partially into receptacle 48, a window 62 provided in the sample cell is optically aligned with the gas monitoring components of the sidestream gas measurement assembly. More specifically, infrared radiation emitted from radiation source 44 passes through window 62 of sample cell 60. Thereafter, the infrared radiation passes through a sample chamber defined in the interior of sample cell 60, where a portion of the radiation is absorbed, or attenuated, by one or more respiratory gases, such as carbon dioxide, or vaporized materials, in the sample chamber. The unabsorbed infrared radiation then passes through another window (not shown) into radiation detector 46, which converts the unabsorbed, or transmitted, infrared radiation into electrical signals.

The present invention also contemplates that the sample cell can include a single window. In which case, the radiation transmitted into the sample chamber and the radiation exiting the sample chamber pass through this common window. A reflective element is provided in the sample cell to allow the radiation to pass back through the window by which it entered the sample cell.

The present invention also contemplates that the sample cell may be either integrated with filter, sampling tubing, or a combination of these two, or removable from the filter and/or sampling tubing. Thus, the sample cell may be either disposable or reusable. A sample cell integral with the sample tubing offers the best construction with respect to maintenance of signal fidelity. However, integrating the sample cell with the sample tubing is not required according to the present invention.

Sidestream gas measurement assembly preferably includes a processor (not shown) for controlling radiation source 44 and for processing the signals from radiation detector 46. In an exemplary embodiment of the present invention, an output device 54, such as an LCD or meter, is provided on housing 42 for visually displaying the result of the gas sampling measurements determined by the processor and/or the radiation detector, such as a determination of the amount of the monitored gas or vaporized material in the patient's respiration or the partial pressure of the monitored gas.

The present invention also contemplates that sidestream gas measurement assembly 40 communicates, or interfaces, with other equipment, such as a host system, by way of one or more hard wired or wireless communication links, as known in the art. By way of example only, sidestream gas measurement assembly may have a cable 56 connected thereto and in communication with one or more components of the sidestream gas measurement assembly, such as radiation source 44, radiation detector 130, the processor (not shown) or the like. It is known, for example, to provide an optional barometric pressure compensation in a host system that can be used, for example, to calculated the % $CO_2$ in the patient's respiration.

Sidestream gas measurement assembly 40 includes a system for aspirating gas from the sample site into the sampling tube and, hence, into the sample cell. More specifically, a pump 58 is provided in housing 42 that selectively couples to an outlet port of the sample cell for pulling gas through the sample cell from the sample site. A scavenging port 59 is coupled to the pump to allow the gas drawn through the sample cell by the pump to be discharged from the sidestream gas measurement assembly. The present invention contemplates that pump 58 is activated when the sample cell is connected to the sidestream gas measurement assembly and deactivated when it is removed. Of course, any pump activation and deactivation technique, manual or automatic, can be used with this invention To perform gas monitoring using sidestream gas sampling system 30, the user couples a sampling tube 64 in fluid communication with an airway of a patient, for example by attaching a nasal cannula on the patient or an airway adapter in a breathing circuit to which the sampling tube is connected. The sample cell must also be assembled with the sidesteam gas measurement assembly by placing the sample cell in the receptacle in the housing of the sidestream gas measurement assembly. Pump 58 is activated so that gas originating in an airway adapter or nasal cannula is drawn into sampling tube 64 and sample cell 60. One end of the sampling tube is coupled to sample cell 60 such that the interior of tube is in fluid communication with a sample chamber defined in the sample cell.

The partial pressure of one or more gases, such as carbon dioxide, or vaporized materials in the respiration of a patient, is determined using a gas sensing system, which includes radiation source 44, e.g., an infrared radiation source, and radiation detector 46, e.g., an infrared detector. The output of the gas sensing system, for example signals indicative of the partial pressure of one or more gases of vaporized materials, are provide to a processor and output device 54, such as a meter, a liquid crystal display (LCD) screen, or provide to an external device, such as a printer, computer monitor, host system, or other gas monitoring system via a conventional communication link.

After one or more parameters of respiration of such a patient are monitored as discussed above, the sample cell is detached from sidestream gas measurement assembly 40. The sample cell can be reconditioned if it is reusable for repeated use, or it can discarded and a new sample cell can be used.

The present invention contemplates that an optional filter 66 can be provided between sample cell 60 and the airway adapter at the other end of sampling tube 64. In short, a filter can be provided along the length of sampling tube 64 or at its ends. Examples of filters suitable for use with the present invention include a water filter, secretion filter, or any conventional filter that prevents liquid and/or particulates from reaching the sample cell. The present invention also contemplates that optional filter 66 may be a part of sample cell 60 or communicate with exhaust or scavenging port 59 located downstream from sample cell 60. Scavenging port 59 may vent the gas to the atmosphere, connect to a scavenging system, or return the gas to the breathing circuit.

Figure 2A:
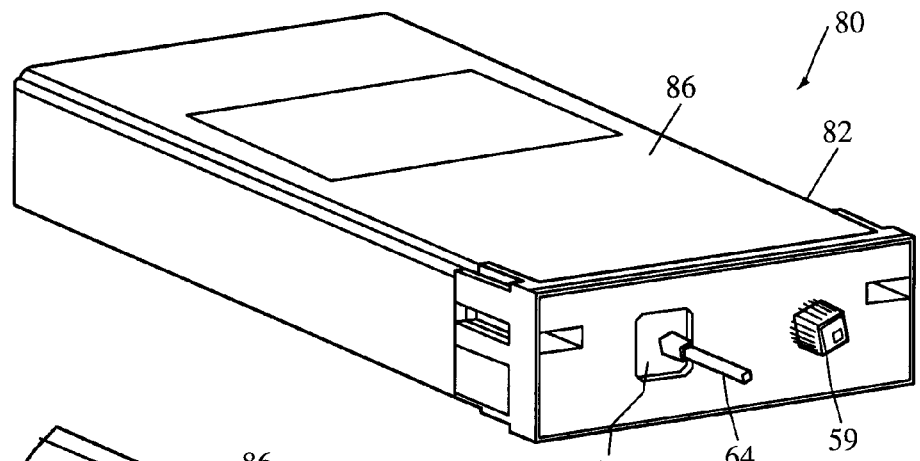
FIGS. 2A-2C are, respectively, perspective and exploded views of a second embodiment of a sidestream gas sampling system that forms a component in a multiparameter monitoring apparatus according to the principles of the present invention.
Figure 2B:
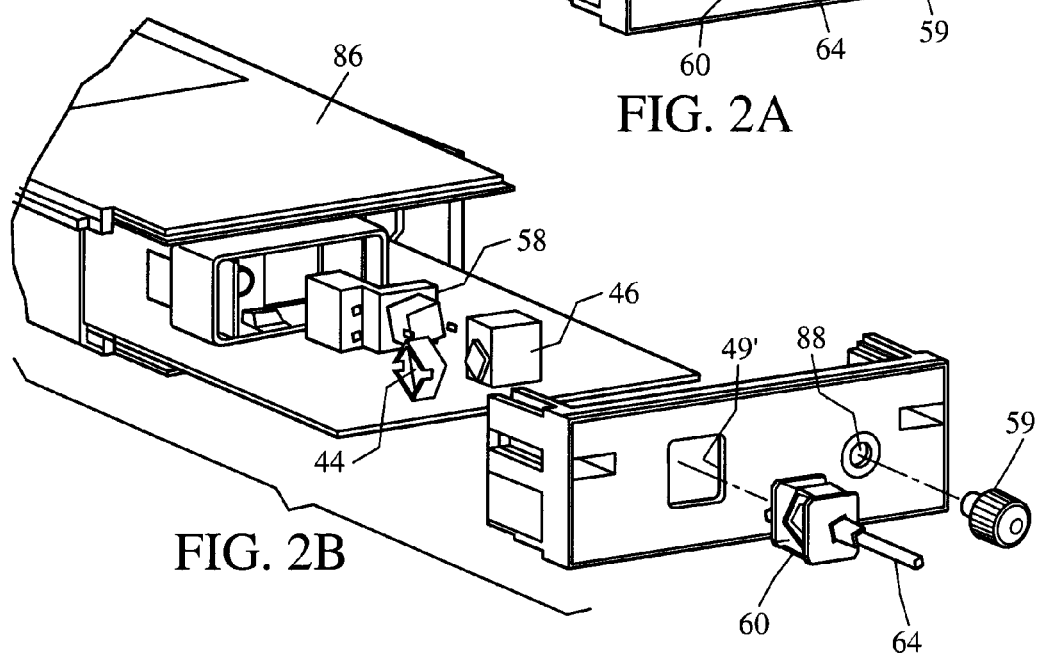
Figure 2C:
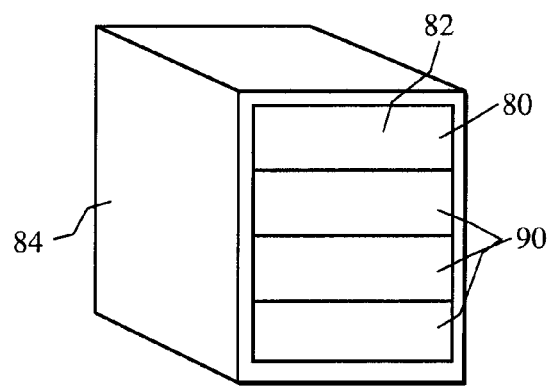

FIGS. 2A-2C illustrate a second embodiment of a sidestream gas sampling system 80. In this embodiment, the sidestream gas sampling system, and, in particular, sidestream gas measurement assembly 82, is a component in a multiparameter monitoring apparatus 84. The components of sidestream gas measurement assembly 82 are generally the same as sidestream gas measurement assembly 40 of FIGS. 1A and 1B. For example, housing 86 of sidestream gas measurement assembly 82 housing contains a gas sensing system, including radiation source 44 and radiation detector 46 and includes a slot 49' into which sample cell 60 is inserted for placing the window of the sample cell in optical alignment with the components of the gas sensing system. An aperture 88 is provided in housing 86 to for scavenging port 59.

As shown in FIG. 2C, sidestream gas sampling system 80 is one of a plurality of modules 90 in multi-parameter monitoring apparatus 84. Thus, sidestream gas measurement assembly 82 is preferably configured and arranged to be coupled to a housing containing modules 90.

Figure 3A:
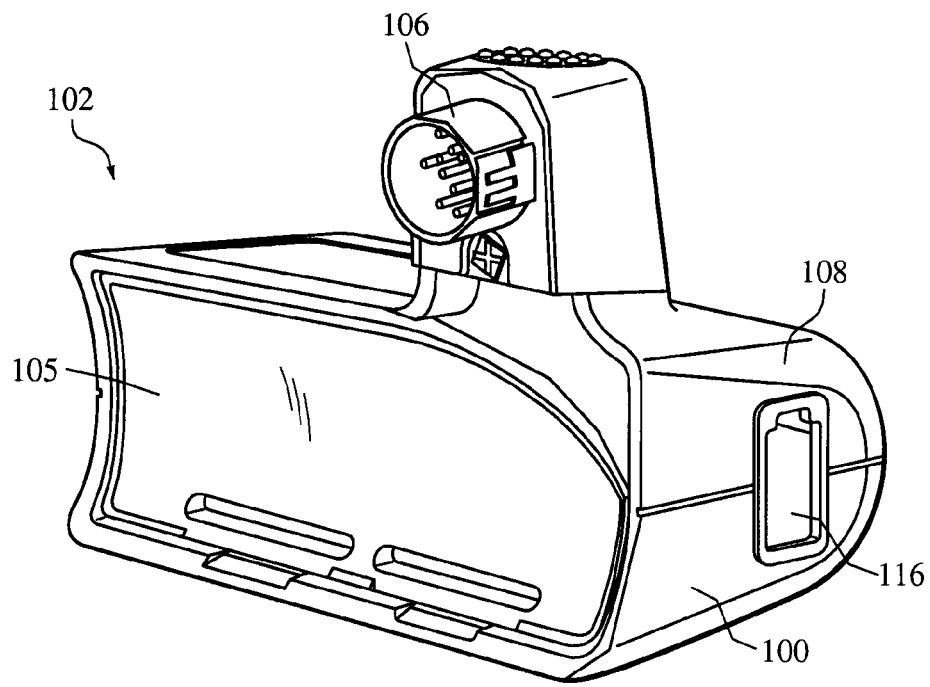
FIGS. 3A and 3B are perspective views and FIG. 3C is an exploded view of third embodiment of a sidestream gas measurement assembly of a sidestream gas sampling system that is adapted to be tightly coupled to a multi-parameter monitoring system.
Figure 3B:
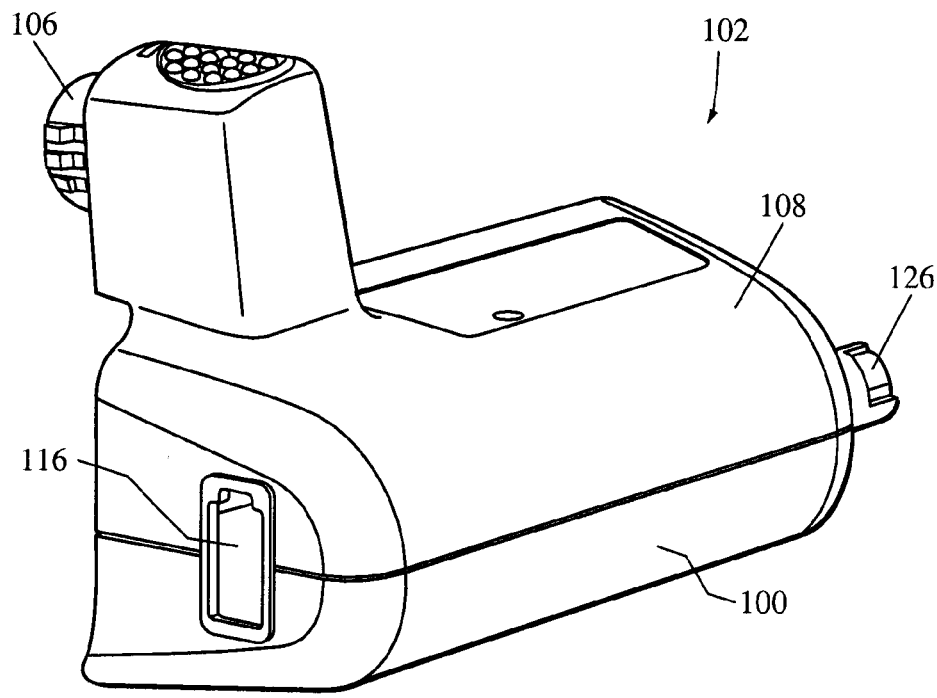
Figure 3C:
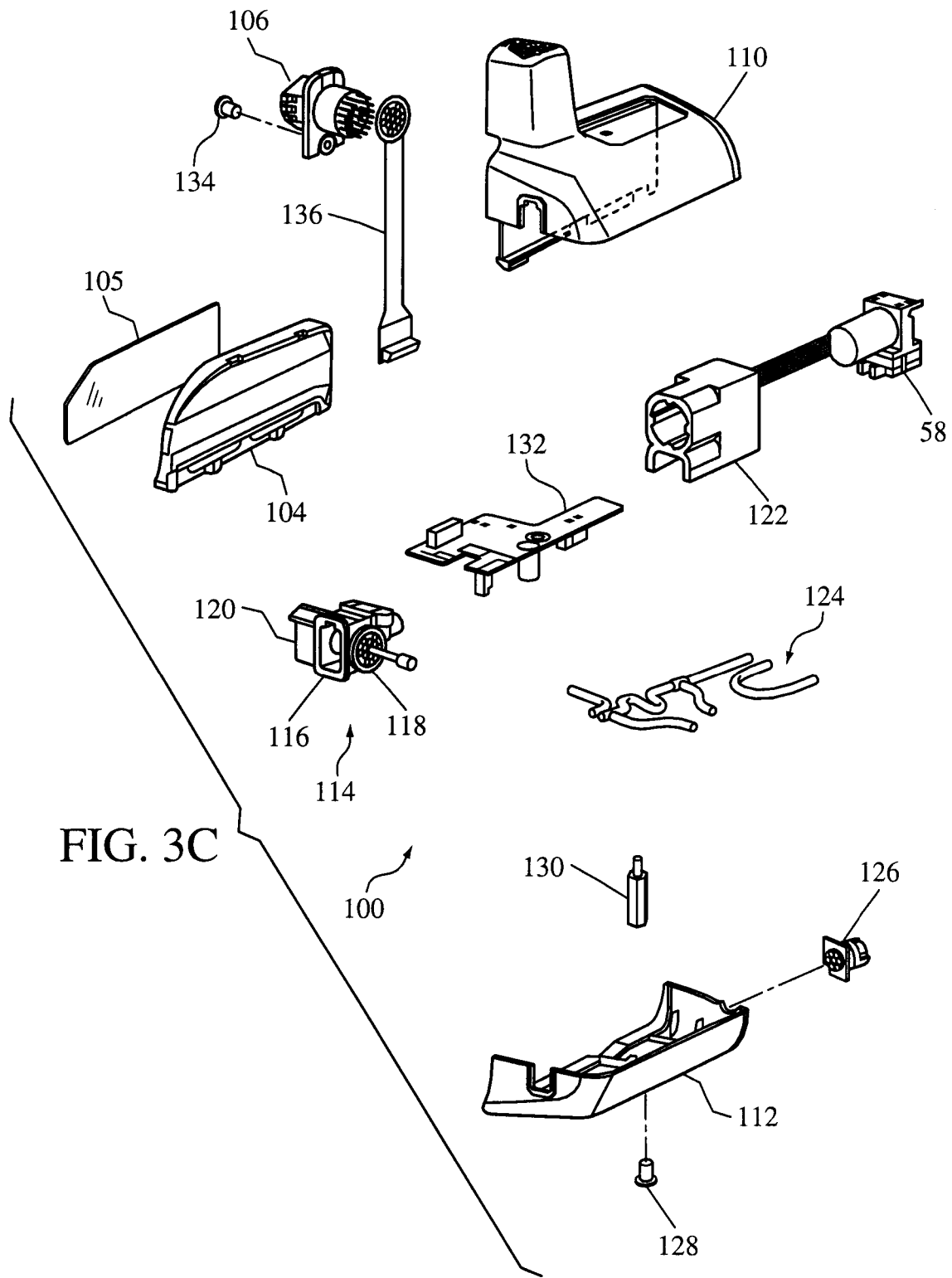
Figure 4E:
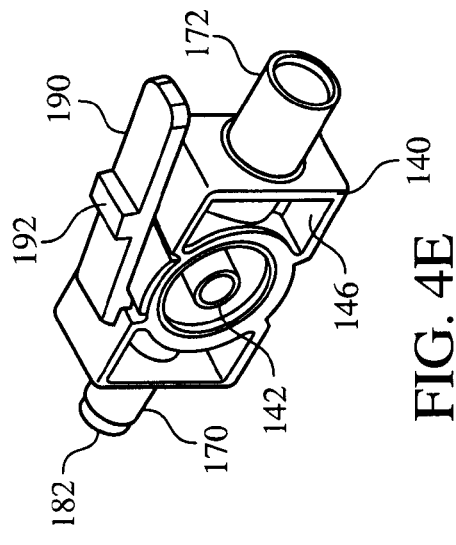
FIGS. 4A-4E are, respectively, top, front, side, rear, and perspective views of an example of a removable sample cell incorporating teachings of the present invention.
Figure 4D:
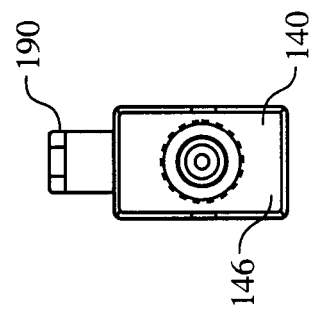
Figure 4A:
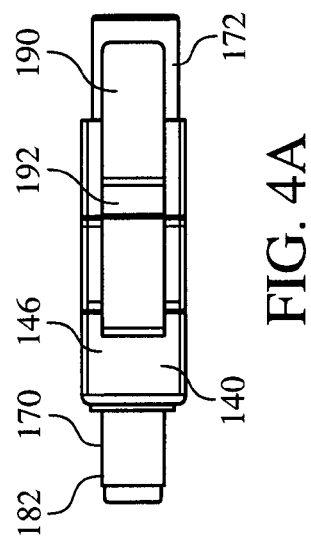
Figure 4C:
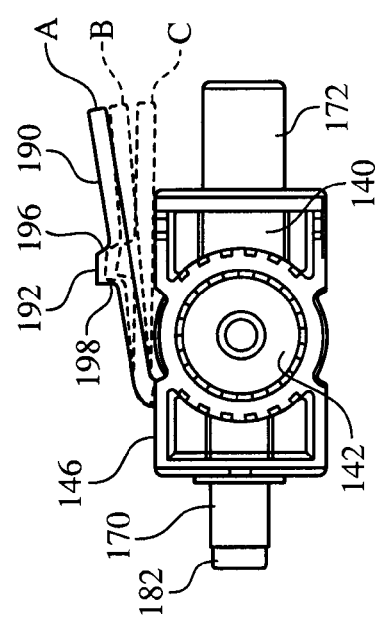
Figure 4B:
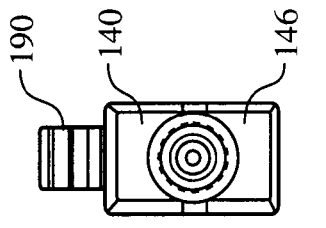

FIG. 3A-3C illustrate a third embodiment of a sidestream gas measurement assembly 100 in a sidestream gas sampling system 102 that is adapted to be coupled to a multi-parameter monitoring system (not shown). Sidestream gas measurement assembly 100 includes a support bracket 104 and monitor connector 106 for coupling the sidestream gas measurement assembly to the remaining components of the multi-parameter monitoring system, which are not illustrated herein, such that the sidestream gas measurement assembly appears to be an integral part of the multi-parameter system, such as an extension of the housing for the multi-parameter system. The present invention contemplates securing support bracket 104 of sidestream gas measurement assembly 100 to the remaining components of the monitor by an adhesive layer 105 as well as connector 106. Sidestream gas measurement assembly 100 includes a housing 108 defined by a first housing portion 110 and a second housing portion 112 that are adapted to be joined together. Interlocking elements can be provided on housing 108 for securing the sidestream gas measurement assembly to the main housing of the multi-parameter system.

Figure 5B:
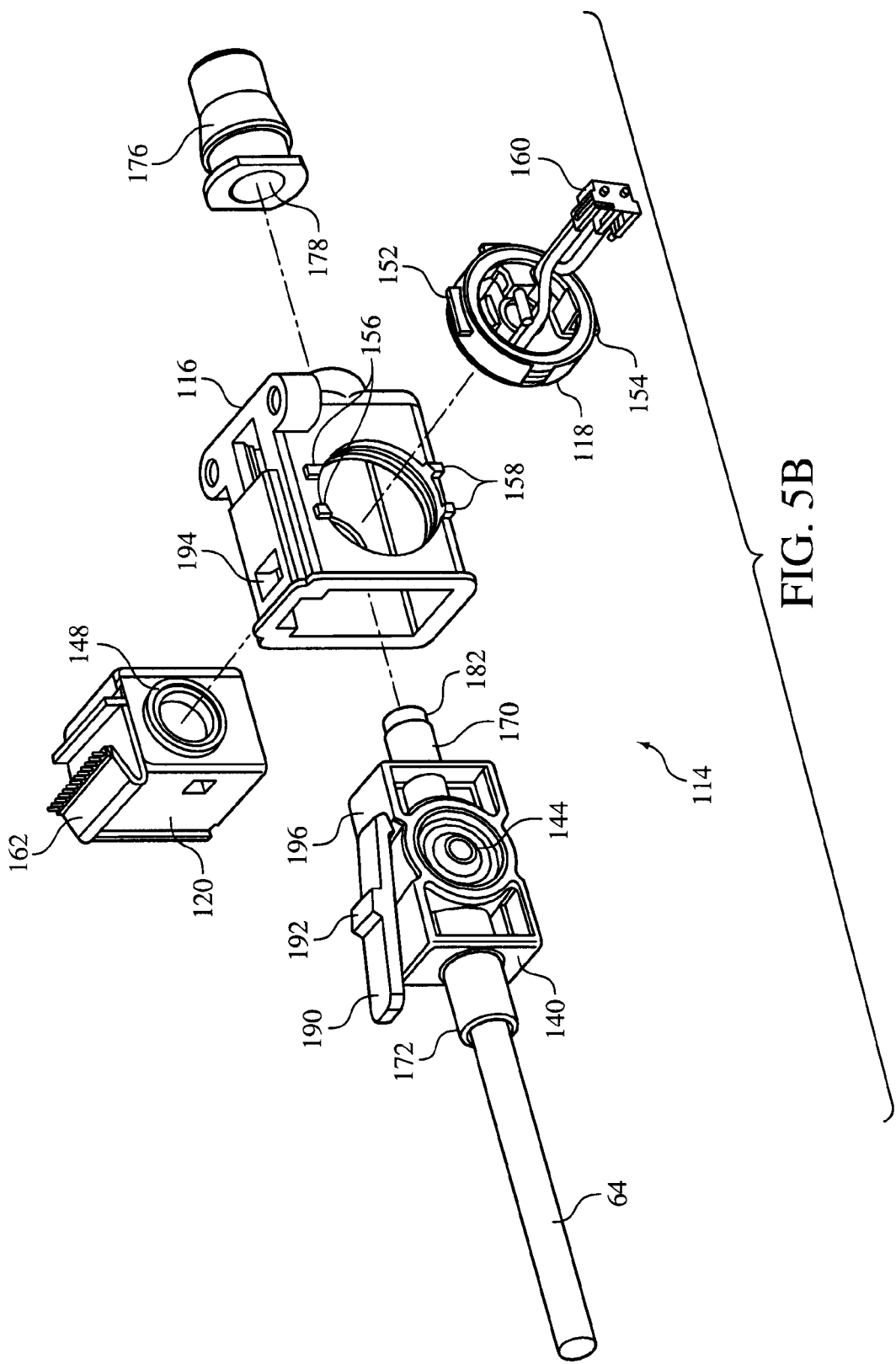

Sidestream gas measurement assembly 100 also includes a gas sensing system, generally indicated at 114, which is illustrated in greater detail in FIGS. 5A and 5B. Gas sensing system 114 includes a sample cell receptacle 116 that receives, at least in part, the sample cell, a radiation source 118 and a radiation detector 120. As in the previous embodiment, when the sample cell is properly assembled with the sidestream monitor, the sample cell is seated in receptacle 116 such that radiation from source 118 passes through a sample chamber in the sample cell and is received by detector 120 after passing through the gas contained in the sample chamber. In this embodiment, receptacle 116 provides a separate, one-piece subassembly that aligns the optics of the gas sensing system and separates these optics from the rest of the components of the sidestream gas measurement assembly.

A pump 58 is provided in sidestream gas measurement assembly 100 to draw gas from the sampling site through the sample cell. To dampen vibrations from the operation of the pump, the pump is placed in an isolation boot 122. A tubing 124 interconnects the pump, sample cell receptacle 116, valving (not shown), and an exhaust port 126. A screw 128 in conjunction with a spacer 130 and the structure of second housing portion 112 securely attaches a circuit board 132 to the second housing portion. A screw 134 attaches monitor connector 106, which interfaces to circuit board 132 via a $CO_2$ flex connector 136 to first housing portion 110.

Figure 6A:
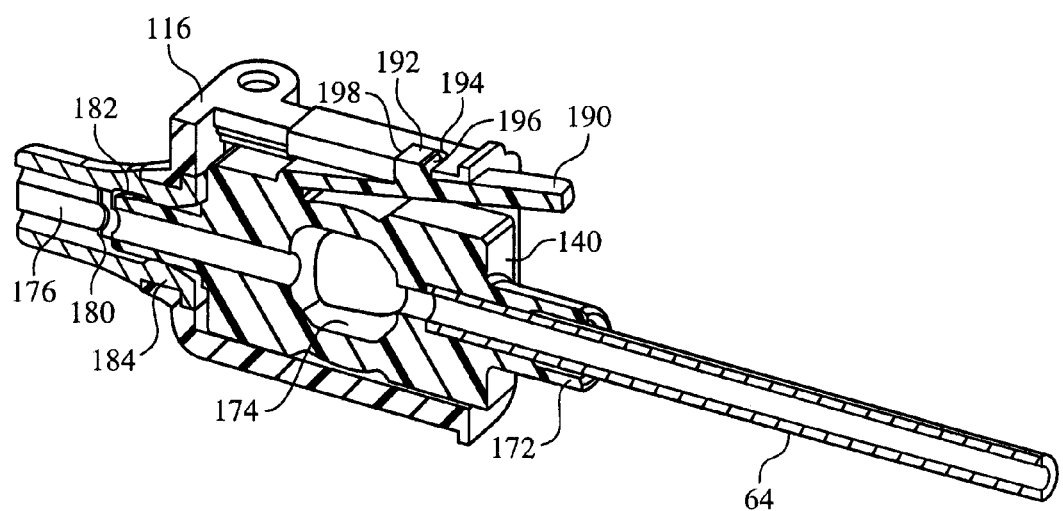
FIG. 6A is a cross-sectional perspective view illustrating an exemplary attachment of the sample cell to a receptacle by means of a latching mechanism.
Figure 6B:
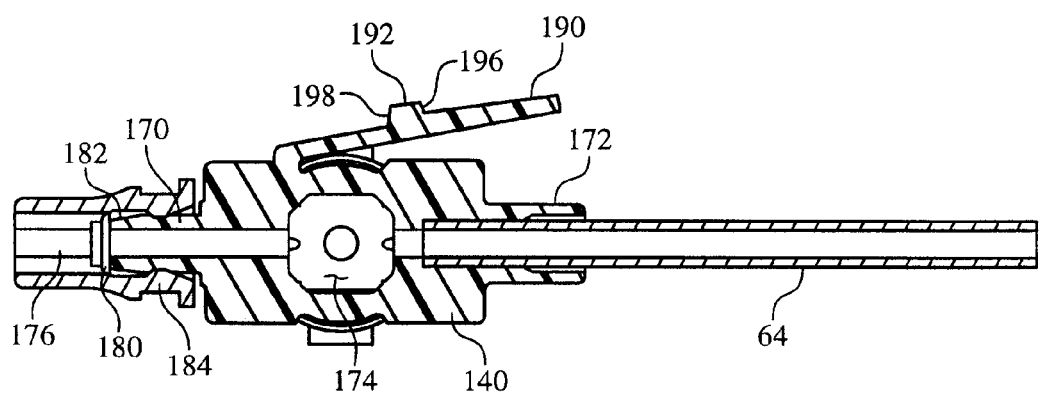
FIG. 6B is a cross-sectional side view illustrating an exemplary attachment of the sample cell to a input port.
Figure 7:
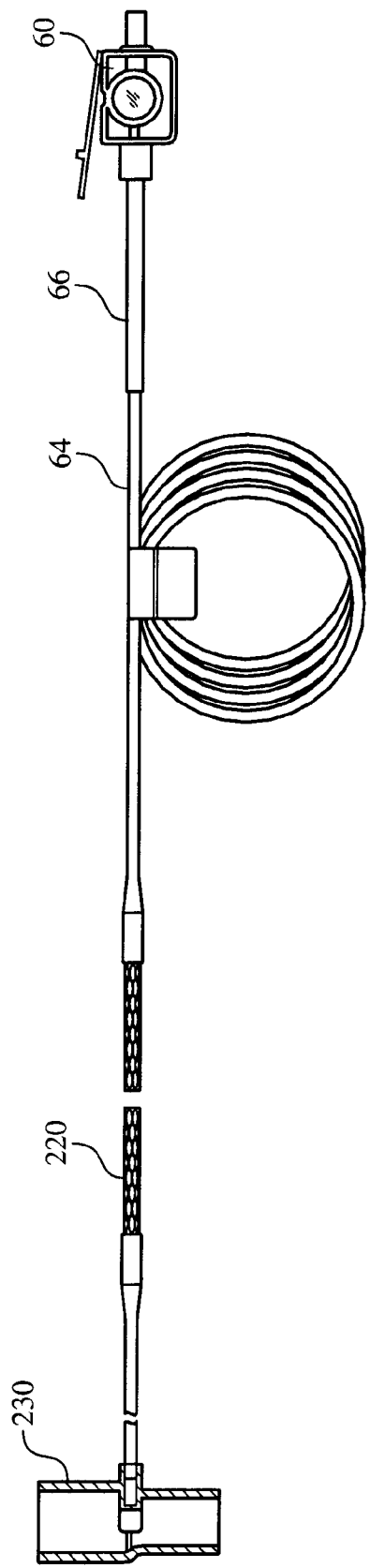
FIG. 7 is a side view of an exemplary pediatric/adult sampling set for use with a humidified breathing circuit, which includes a sample cell, filter, dehumification tubing, and an airway adapter.
Figure 8:
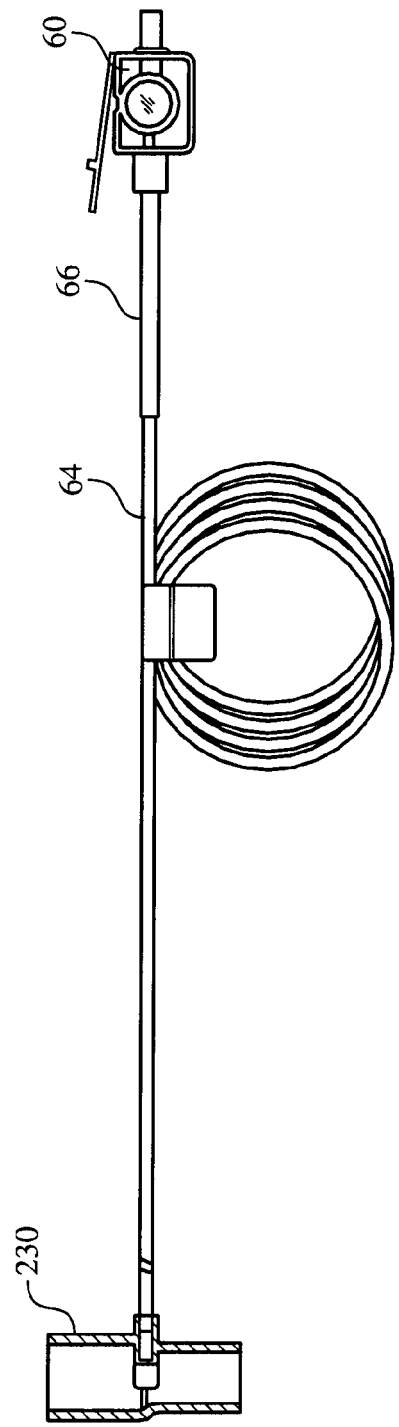
FIG. 8 is a side view of an exemplary pediatric/adult sampling set for use with a non-humidified breathing circuit, which includes a sample cell, a filter, and an airway adapter.

Details of the sample cell, the gas sensing system and a technique for connecting the sample cell to the gas sensing system will now be described with reference to FIGS. 4A-6B. FIGS. 4A-4E illustrate an example of a removable sample cell 140 suitable for use in the sidestream gas sampling systems of the present invention. FIGS. 5A and 5B illustrate an exemplary embodiment of a gas sensing system 114 suitable for use with the various embodiments of the sidestream gas sampling systems of the present invention, which includes sample cell 140. FIGS. 6A and 6B illustrate an exemplary attachment of sample cell 140 to a receptacle in the gas sensing system by means of a latching mechanism.

Sample cell 140 includes a first window 142 and a second window 144 that are configured and oriented on a housing 146 of the sample cell so as to optically align with the components of the gas sensing system, which includes radiation source 118 and radiation detector 120, when the sample cell is assembled with the sidestream gas measurement assembly. Sample cell body 146 may be of a single piece construction, or of a multi-piece construction. Radiation detector 120 and radiation source 118 are preferably affixed to sample cell receptacle 116 using any of a variety of techniques. For example, in the illustrated exemplary embodiment, a boss 148 on radiation detector 120 fits into an opening 150 in sample cell receptacle 116. In this embodiment, boss 148 and opening 150 are circular. It is to be understood, however, that the present invention contemplates other shapes for these elements. Additionally, the rectangular depression that surrounds opening 150 in sample cell receptacle 116 mates with an edge of the rectangular housing of the radiation detector. Tabs 152 and 154 on radiation source 118 fit securely between rectangular boss pairs 156 and 158, respectively, on receptacle 116. Connectors 160 and 162 provide electrical interfaces for the source and detector, respectively. Of course other ways to coupled these components in proper alignment are possible, and would be readily discerned by one skilled in the art.

Sample cell 140 also includes an output port 170 and an inlet port 172, both of which are in fluid communication with a sample chamber 174 defined in sample cell body 146. Gas sensing system 114 includes a pneumatic coupling 176 having an input port 178 and a seal 180. Pneumatic coupling 174 connects output port 170 of sample cell 140 to the pump in the sidestream gas measurement assembly. In the illustrated exemplary embodiment of the present invention the end portion of output port 140 includes a taper 182 to allow the output port to be securely seated against seal 180 of pneumatic coupling 176 and provides a good seal when the sample cell is latched in place on the sidestream gas measurement assembly. A taper is also provided on the interior of end portion 184 of coupling 176 to facilitate coupling of the sample cell and the pneumatic coupling. Proper seating of output port 140 with the input port 178 of pneumatic coupling 174 is important so that a known negative pressure can be applied to the sample chamber generating the desired flow rate of gas through the sample cell.

Sample cell 140 includes an interconnection element 190 a coupled to sample cell body 146 that engages a corresponding feature of the sidestream gas measurement assembly, such as receptacle 116 so that the sample cell is securely and releasably coupled with the sidestream gas measurement assembly 100 and in optical alignment with the optical components of the gas sensing system. In the illustrated exemplary embodiment, interconnection element 190 is a latching arm formed on the upper surface of sample cell body 146. Insertion of sample cell 140 into receptacle 116 deflects latching arm from its original position through positions indicated by letters A, B, and C in FIG. 4C. The latching arm includes a protrusion 192 that engages an opening 194 defined in receptacle 116, thereby securing the sample cell in the receptacle. For operator feedback, an audible clicking sound may be generated by the insertion of the latching arm into the receptacle of the sidestream gas measurement assembly.

To remove sample cell 140 from receptacle 116, latching arm 190 is depressed and pivots downward to release protrusion 192 from opening 194 so that the sample cell can be then removed from the receptacle. In this manner, receptacle 116 properly aligns radiation source 118, radiation detector 120, and sample cell 140 in a repeatable manner. The latching feature provided by interconnection element 190, utilizing a chamfered protrusion 192 located on the latching arm extending from the sample cell interfacing with slot 194 in receptacle 116, compensates for manufacturing tolerance variations in the size of the sample cell body and/or the size of the opening into which the sample cell is inserted. This latching feature also precisely aligns the sample cell in the receptacle in a repeatable fashion.

In the illustrated embodiment, chamfered protrusion 192 is located on latching arm 190 and slot 194 is a rectangular feature located on receptacle 116. The chamfered protrusion 192 is longer than slot 194 so that the protrusion is forced to center itself on a front chamfer 196 and back chamfer 198 when snapped in place. This feature is similar to a taper fit, which is well known in the art compensates for manufacturing tolerances, because the centerline of the chamfered protrusion 192 will always be aligned with the centerline of slot 194. Therefore, variances in dimensions due to molding, for example, will only cause a deviation in the amount of flex in the latching arm. It can be appreciated that proper alignment of the measurement optics with the optical apertures is important so that sufficient radiation passes through the gas within the sample cell to the detector assembly and that a constant path length between the source assembly and detector assembly would be maintained.

The present invention contemplates that the sidestream gas measurement assembly includes a photo-detector or other device that detects when the sample cell is present, for example, to control the operation of the sidestream gas measurement assembly. The present invention also contemplates that the sample cell may include an identification element that is detected by the sidestream gas measurement assembly to provide the sidestream gas measurement assembly with information concerning the sample cell. For example, the identification element can include identifying information indicating the type of sample cell and/or any components associated therewith, e.g., the sampling tube, water trap, etc., and, possibly, any calibration information specific to the sample cell or any components associated therewith. Such identification may be implemented mechanically, optically, magnetically, by way of radiofrequency (RF) signals, or as otherwise known.

Other alternative structures for the invention presently contemplated include, but are not limited to, rounded arched protrusion instead of the chamfered surfaces discussed above. In addition, the interconnection element can be provided at other locations on the sample cell, or multiple interconnection elements can be used. Alternatively, the interconnection element can extend from the receptacle or other component of the sidestream gas measurement assembly and engage a slot, groove or other receiving element defined in the sample cell, effectively reversing the arrangement shown in FIG. 6A. Similarly, the arrangement of protrusion 192 and opening 194 can be reversed.

Improved alignment allows for more consistency in the performance of the device. This device is simple to use and provides both familiar and intuitive operations for insertion and removal of the sample cell. Additionally, the single molded piece of the receptacle allows for a low cost and easy mounting of the optics.

Figure 9:
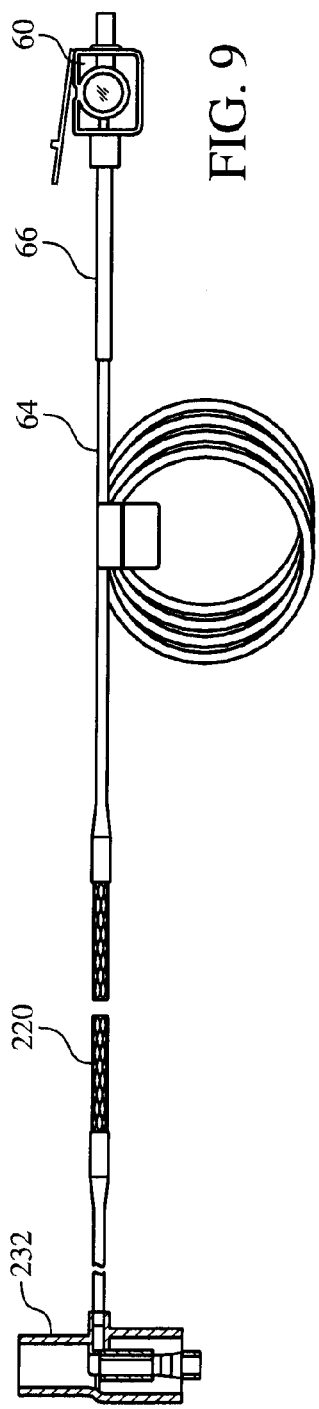
FIG. 9 is a side view of an exemplary neonatal sampling set, including a sample cell, a filter, dehumificiation tubing, and a low deadspace airway adapter.
Figure 10:
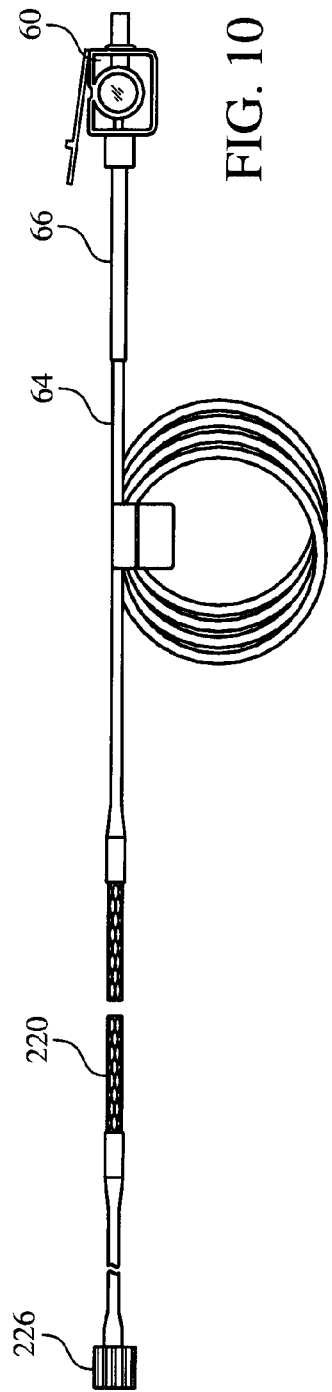
FIG. 10 is a side view of an sampling set for a humidified breathing circuit, including a sample cell, a filter, dehumification tubing, and a Luer fitting.
Figure 11:
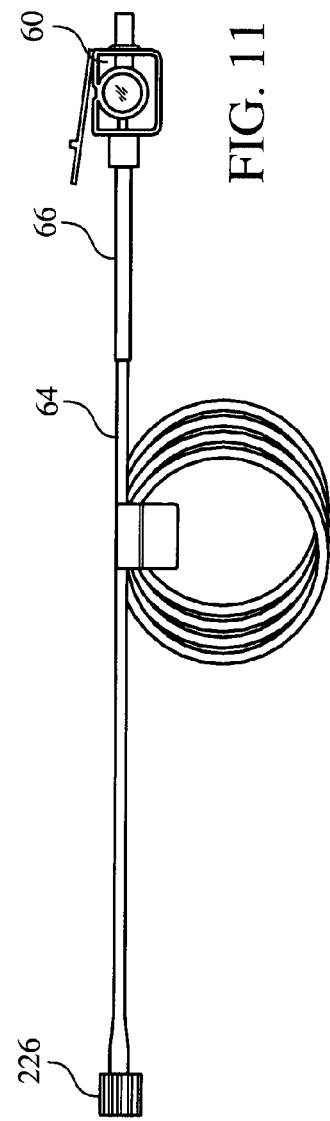
FIG. 11 is a sideview of still another example of a sidestream sampling set.

FIGS. 7-13 depict various sample sets that incorporate teachings of the present invention, each of which includes a sample cell, such as sample cell 60 depicted in FIGS. 1A-4E, and sampling tube 64. These sample sets may be configured for use in one or more sidestream monitoring systems, and may include various additional features, such as a filter 66, dehumidification tubing 220, oxygen delivery tubing 224, Luer fitting 226 and the like. The sample sets may be interfaced to the patient's airway by a nasal cannula 228 (FIGS. 12 and 13), a airway adapter 230 (FIGS. 7 and 8) and low deadspace airway adapter 232 (FIG. 9).

A system incorporating teachings of the present invention may include a reusable or disposable sample cell and a set of sampling tubes, each sampling tube being compatible with the sample cell and different types of airway adapters and/or monitoring apparatus. Exemplary configurations of sampling systems or sets for intubated patients according to the present invention include, but are not limited to:

Adult—humidified (sample cell, filter, dehumidifying tubing, airway adapter);
Adult—non-humidified (sample cell, filter, airway adapter);
Neonatal (sample cell, filter, dehumidifying tubing, low deadspace airway adapter);
Generic—humidified (sample cell, filter, dehumidifying tubing, luer fitting); and
Generic—non-humidified (sample cell, filter, luer fitting).

Exemplary configurations of sampling systems or sets for non-intubated patients with and without $O_2$ delivery include, without limitation:

Adult (sample cell, filter, nasal cannula);
Pediatric (sample cell, filter, nasal cannula);
Infant (sample cell, filter, nasal cannula);
Adult (sample cell, filter, nasal cannula, $O_2$ port); and
Pediatric (sample cell, filter, nasal cannula, $O_2$ port).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A sidestream gas sampling system, comprising:
   (1) a sidestream gas measurement assembly, comprising,
      (a) a housing,
      (b) a radiation source disposed in the housing,
      (c) a radiation detector disposed in the housing,
      (d) a receptacle defined in the housing, and
      (e) a first alignment mechanism associated with the receptacle; and
   (2) a sample cell assembly adapted to be coupled to the sidestream gas measurement assembly, the sample cell assembly comprising:
      (a) a sampling tube have a first tube end portion adapted to be disposed in fluid communication with an airway of a patient and a second tube end portion, wherein the sampling tube carries a gas sample from the first tube end portion to the second tube end portion, and wherein the gas sample is a fraction of a total gas flow to or from the patient,
      (b) a sample cell having a first cell end portion coupled to the second tube end portion of the sampling tube, the sample cell further having a second cell end portion substantially opposite the first cell end portion of the sample cell,
      (c) a sample chamber defined in the sample cell for receiving a respiratory sample from the patient via the sampling tube,
      (d) a first window defined in the sample cell, and
      (e) a second alignment mechanism associated with the sample cell, wherein the first alignment mechanism and the second alignment mechanism cooperate to enable the sample cell to be inserted into the receptacle in a proper orientation, wherein the second alignment mechanism comprises a latching arm extending from a region near the second cell end portion of the sample cell towards the first cell end portion of the sample cell, and wherein the latching arm forms an acute angle with the region near the second cell end portion of the sample cell.

2. The sidestream sampling system of claim 1, wherein the radiation source comprises a source of at least one wavelength of infrared radiation, and wherein the radiation detector is configured to detect at least one wavelength of infrared radiation.

3. The sidestream sampling system of claim 1, further comprising a second window disposed in the sample cell such that the first window and the second window are on opposite sides of the sample cell.

4. The sidestream sampling system of claim 1, wherein the sidestream gas measurement assembly further includes a processor operatively coupled to at least one of the radiation source and the radiation detector.

5. The sidestream sampling system of claim 1, wherein the sidestream gas measurement assembly further comprises at least one communication link for establishing communication with a component external to the sidestream gas measurement assembly.

6. The sidestream sampling system of claim 1, wherein the sample cell assembly further comprises a filter positioned along the sampling tube.

7. The sidestream sampling system of claim 1, wherein the first alignment mechanism has a slot defined in a wall of the receptacle and the second alignment mechanism further comprises a protrusion extending from the latching arm for snapping into the slot.

8. The sidestream sampling system of claim 7, wherein the sample cell assembly further comprises a first locking member associated with the slot and a second locking member associated with the protrusion.

9. The sidestream sampling system of claim 1, wherein the sample cell assembly further comprises a first locking member associated with the receptacle and a second locking member associated with the second-sample cell.

10. The sidestream sampling system of claim 1, wherein the receptacle has a rectangular shaped opening into which the sample cell inserts.

11. The sidestream sampling system of claim 10, wherein the opening is defined in a surface of the housing and is flush with the surface.

12. The sidestream sampling system of claim 1, wherein the sample cell further comprises an outlet port disposed on the second cell end portion of the sample cell.

13. The sidestream gas sampling system of claim 1, wherein the sidestream gas measurement assembly further comprises a pump disposed in the housing and adapted to draw the fraction of the total gas flow into the sampling tube.

14. The sidestream gas sampling system of claim 1, wherein the latching arm is configured to move in a direction substantially perpendicular to a longitudinal axis of the sample cell.

15. A method of sidestream respiratory analysis, comprising the acts of:
   providing a sample cell assembly comprising (a) a sampling tube have a first tube end portion and a second tube end portion, and (b) a sample cell having a first cell end portion coupled to the second tube end portion of the sampling tube, the sample cell further having a second cell end portion substantially opposite the first cell end portion of the sample cell;
   placing the first tube end portion of the sampling tube in fluid communication with an airway of a patient;
   carrying a gas sample from the first tube end portion to the second tube end portion, wherein the gas sample is a fraction of a total gas flow to or from the patient;
   orienting the sample cell such that a first alignment mechanism associated with a receptacle defined in a housing of a sidestream gas measurement assembly is aligned with a second alignment mechanism associated with the sample cell;
   inserting the sample cell into the receptacle responsive to the first alignment mechanism and the second alignment mechanism being properly oriented relative to one another, wherein the second alignment mechanism comprises a latching arm extending from a region near the second cell end portion of the sample cell towards the first cell end portion of the sample cell, and wherein the latching arm forms an acute angle with the region near the second cell end portion of the sample cell; and
   analyzing a parameter of the gas sample using the sidestream gas measurement assembly.

16. The method of claim 15, further comprising removing the sample cell from the receptacle after completing the analyzing act.

17. The method of claim 15, wherein the act of placing the first tube end portion of the sampling tube in fluid communication with the airway of the patient comprises at least one of the acts of:

placing a nasal cannula on the patient in fluid communication with the airway of the patient, wherein the nasal cannula communicates with the sampling tube; and positioning an airway adapter along a breathing circuit operatively coupled to the airway of the patient and connecting the first tube end portion of the sampling tube to a port disposed on the airway adapter.

18. The method of claim 15, wherein the act of analyzing the parameter comprises analyzing at least one of gas and vaporized material present in a gas in a respiration of the patient.

19. The method of claim 18, wherein the act of analyzing the parameter comprises analyzing an amount of at least one of carbon dioxide and oxygen present in the respiration of the patient.

20. The method of claim 15, further comprising the act of reading identifying information from the sample cell responsive to the sample cell being assembled with the sidestream gas measurement assembly.

* * * * *